United States Patent [19]

Burns

[11] Patent Number: 4,840,908

[45] Date of Patent: Jun. 20, 1989

[54] CULTURE BOTTLE ASSEMBLY

[75] Inventor: James A. Burns, Elizabeth, N.J.

[73] Assignee: Becton, Dickinson and Company, Franklin Lakes, N.J.

[21] Appl. No.: 217,481

[22] Filed: Jun. 29, 1988

[51] Int. Cl.$^4$ ............................................. C12M 1/24
[52] U.S. Cl. .................................. 435/296; 435/284; 435/299; 215/227
[58] Field of Search ............... 435/296, 287, 284, 299; 215/227, 277, 276

[56] References Cited

U.S. PATENT DOCUMENTS

| | | | |
|---|---|---|---|
| 3,589,983 | 6/1971 | Holderith et al. | 195/139 |
| 3,651,926 | 3/1972 | Elfast, Jr. . | |
| 3,701,717 | 10/1972 | Inguorsen | 435/296 |
| 4,308,347 | 12/1981 | Forrer et al. | 435/34 |
| 4,665,035 | 5/1987 | Tunac | 435/296 |
| 4,678,753 | 7/1987 | Hempel et al. | 435/296 |

Primary Examiner—Larry Jones
Attorney, Agent, or Firm—Robert P. Grindle

[57] ABSTRACT

A culture bottle assembly is provided with an upright support carrying an agar slant surface arranged to be exposed, intermittently, to a body fluid sample and a nutrient broth to culture on the slant potential organisms contained in the sample. The arrangement is such that the support with the slant is not only easily exposed to the sample and broth for culturing, but also may be segregated easily from the assembly so that, after an appropriate incubation period, the slant may be exposed completely for direct examination. The assembly may include a dual upright support surface in order to afford a larger surface for greater separate culture development on a solid media or more than one solid medium.

10 Claims, 2 Drawing Sheets

CULTURE BOTTLE ASSEMBLY

BACKGROUND AND STATEMENT OF THE INVENTION

This invention relates to a device for the detection of microorganisms in a fluid sample such as, for example, body fluids. More particularly, this invention relates to a device containing an agar slant as the solid medium in combination with a connection for the device to a liquid medium culture bottle or container. The device provides for proper exposure of the two media to the sample under investigation while at the same time providing complete non-covered access to the solid agar slant. Thus, once the microorganisms have been grown, they may be examined directly without any glass or plastic covering interfering with the examination.

In the detection of microorganisms in body fluids, particularly bacteria in blood, there is a requirement that a sample of the fluid be used to inoculate a liquid nutrient medium. Subsequent to this, the liquid medium is in turn used to inoculate a solid medium to continue the growth of the organisms. Generally, devices have been provided in which both the liquid and the solid culture media are combined in the same container. This overcomes any problems involving exposure during transfer of these cultures in the liquid medium to the solid culture medium in another container. Representative of such devices is that described in U.S. Pat. No. 3,589,983, issued June 9, 1971. Other patents directed to the subject matter of the invention include U.S. Pat. No. 3,651,926, issued Mar. 28, 1972 and U.S. Pat. No. 4,308,347, issued Dec. 29, 1981.

There are problems, however, with combined devices in that the constituents of the solid medium may be dissolved in the liquid medium. Thus, only solid media compatible with the liquid medium can be utilized. If the solid media constituents pass into the liquid medium, differentiations of the pathogens may no longer be possible.

With the present invention, the solid medium and the liquid medium are appropriately separated, but may be connected together in order to provide the proper exposure of the solid medium to the liquid medium containing the sample under consideration. Nevertheless, once the inoculation period has taken place, the device of the invention may be disassembled to the extent whereby the solid medium agar slant may be examined completely and directly without any interference from some covering therefor.

That is, the device of the invention includes a base structure supporting an agar slant, for example. The base structure includes a connection for connecting the base structure to a liquid culture medium container. The base structure carrying the agar slant, which has the solid medium contained thereon, has a complete covering or cap for covering the solid medium in a liquid-tight connection so that once the sample has been introduced into the liquid medium container, the device of the invention may be connected thereto and the agar slant or solid medium may be exposed to the liquid medium containing the sample of interest.

Nevertheless, the exposure is only intermittent, as required and desired, in order to provide the appropriate culture development during the inoculation period, with proper removal of the liquid medium, intermittently, in order to allow the culture to take place on the solid agar slant. Once the inoculation period has taken place, the entire cover on the device may be removed so that the entire agar slant and/or solid media with the cultured organisms present thereon may be exposed for complete examination by the laboratory technician.

Other objects and advantages of the invention will be apparent from the following description, the accompanying drawings, and the appended claims.

DETAILED DESCRIPTION OF THE INVENTION

Figure 1:
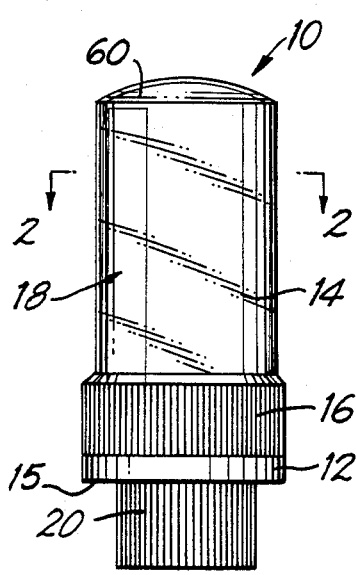
FIG. 1 is a view in elevation of a device illustrating the invention.
Figure 3:
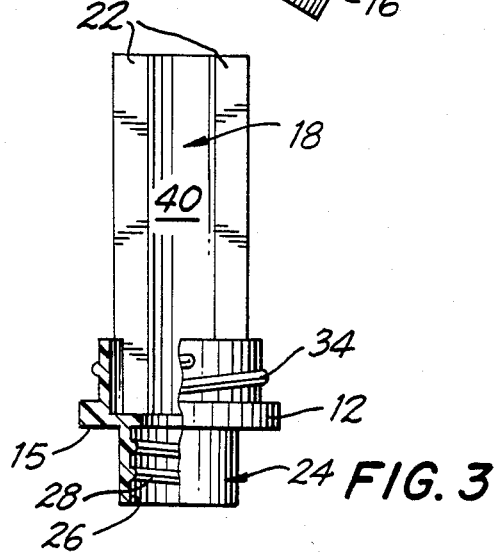
FIG. 3 is a partial sectional view of the device of FIG. 1 with the overlying cap removed.
Figure 4:
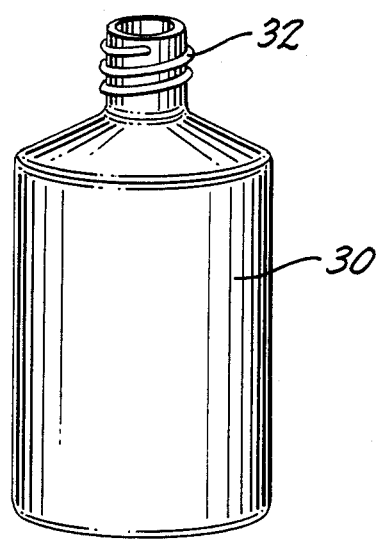
FIG. 4 is a perspective view of a liquid medium container representative of the type to which the device of the invention is attached for culturing.

Referring to the drawings in which like reference numerals refer to like parts throughout the several views thereof, in FIG. 1 the reference numeral 10 designates the device of the invention having a base 12 upon which a solid medium upright support 18 is mounted. Support 18 has a surface 40 for the solid medium which may be an agar slant. Positioned over base 12 and support 18 is an elongated cap 14 which is screwed onto base 12 with threads 34, as shown in FIG. 3. Cap 14 includes a knurled surface 16 for ease of mounting and removal of cap 14 from base 12. Integral with base 12 on the bottom surface 14 thereof is an annular extension 24 with an opening 26 for connection to a conventional liquid culture medium bottle 30. Extension 24 has a cover 20 frictionally engaging the outer surface to protect opening 26 prior to use. As can be seen in FIG. 3, the extension 24 includes on the internal surface of opening 26 thereof threads 28 for cooperating with threads 32 on the neck of a culture bottle 30, as shown in FIG. 4.

Figure 2:
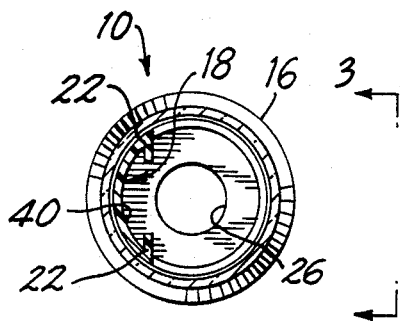
FIG. 2 is a cross-sectional view taken along lines 2—2 of FIG. 1.
Figure 7:
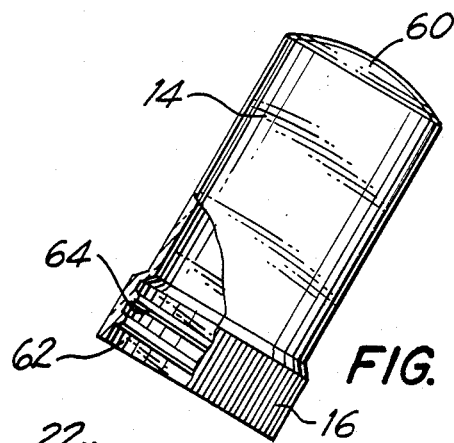
FIG. 7 is a partial sectional view of the elongated cap shown separately from the device of the invention.

Referring now to FIG. 2, a sectional view of the arrangement shown in FIG. 1 is shown. FIG. 2 shows the generally U-shaped configuration of support 18 with the opposed integral extensions or flanges 22 defining active surface 40 upon which the solid culture medium may be placed for subsequent use. FIG. 7 shows cap 14 removed from base 12. As can be seen in FIG. 7, cap 14 has a closed top end 60 and an open end 62 for receiving upright support 18. Internally of cap 14, adjacent the open end thereof are internal threads 64 for cooperating with threads 34 on base 12.

Figure 5:
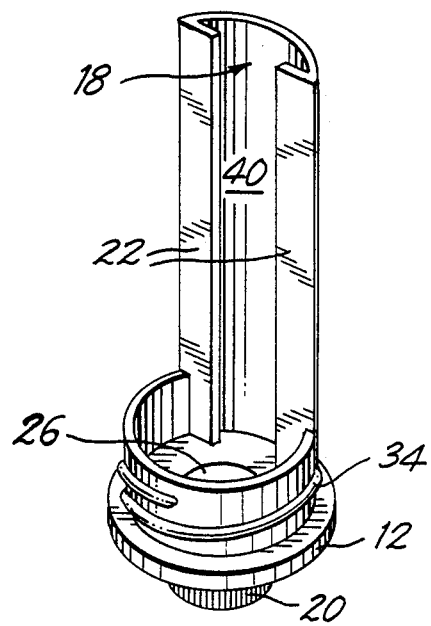
FIG. 5 is a perspective view of the device of the invention with the cap removed.

Referring now to FIG. 5, a perspective view of the device of FIG. 1 is shown. As can be seen in this view, surface 40, for placing the solid culture media, is generally u-shaped in configuration with the opposed extensions or flanges 22 serving to confine to a certain extent the solid media surface 40. Thus, when the device 10 is mounted on the culture bottle 30 containing a liquid medium and the sample of interest, through the connection of threads 28 with threads 32, and the bottle and device 10 of the invention are inverted to allow the liquid to flow over surface 40, the opposed flanges 22 have the effect of preventing any undue turbulence over the surface 40 during this exposure to the liquid contained in bottle 30. During use, once a sample of interest has been introduced into the bottle 30 and the connection made, as discussed above, the device 10 and bottle 30 are inverted periodically over a period of time, as required by the particular solid and liquid media being used, until the incubation period has passed for development of the desired growth of organisms.

Figure 6:
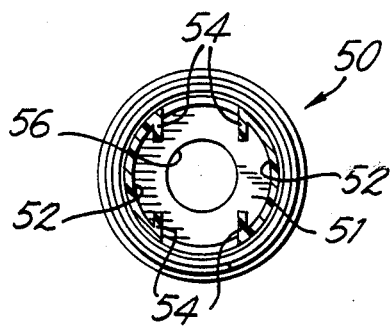
FIG. 6 is a sectional view of a further embodiment of device of the invention illustrating a dual agar slant arrangement.

Referring now to FIG. 6, a cross-sectional view is shown of a device 50 which is another embodiment of the invention in the form of a dual upright support arrangement with two opposed supports 52 having opposed flanges 54 on either side of base 51 of device 50. Thus, with the arrangement in FIG. 6, two different solid culture media may be applied on the two different supports 52 of device 50. Alternatively, with this device, because of the increased extent of the effective surface area 52 for the dual configuration, a larger quantity of organisms may be cultured during a single incubation period. FIG. 6 shows bore 56 at the bottom of base 51 of the device 54 for connection in the same manner as device 10 to a culture bottle.

In either form of embodiments shown above, the device thus formed is then tilted several times to guarantee optimum contact between the liquid and the solid nutrient media. The apparatus may then be incubated at a temperature of, for example, within the range of between about 20° C. and 37° C. for from one hour up to perhaps ten days after which the growth present on the media is observed and evaluated. In this connection, it should be understood that the cap 14 of device 10 of the invention is transparent so that the contents of an agar slant on surface 40 may be readily observed during the period of inoculation without opening the device. For this reason, if no growth can be detected, the incubation process can be repeated several times. In cases of longer incubations, for example, the device may be tipped at least once a day to guarantee optimum contact between the liquid and solid nutrient media.

Thus, as will be appreciated from the above description, there is provided in accordance with this invention, a device for culturing organisms wherein both solid and liquid culture media are required, with the device being particularly appropriate for examination of organisms developed during the incubation period of the device. That is, the device provides for removal of the entire cover of the support carrying the solid media so that the cultured organisms may be readily observed without any obstruction or covering thereover.

Moreover, the assembly is comprised of moldable parts of thermoplastic materials which may be mass produced, as will be understood, from a variety of materials including, for example, polyethylene, polypropylene, and polycarbonate.

While the forms of apparatus herein described constitute preferred embodiments of the invention, it is to be understood that the invention is not limited to these precise forms of apparatus and that changes may be made therein without departing from the scope of the invention which is defined in the appended claims. For example, whereas one form of arrangement is shown wherein the device of the invention is in a circular or tubular form, it is to be understood that the device may be comprised of a square cap structure and square base containing are upright support with an agar slant thereon. The limitation is only that the device cap be transparent for ready observation of the solid media for the development of organisms thereon during the incubation period so that the user will know when the cap may be removed for complete direct observation of the developed organisms.

What is claimed is:

1. A device for culturing microorganisms wherein the sample of interest is to be exposed separately to both a solid and a liquid culture medium; characterized by
   (a) a generally flat base;
   (b) said base having an upper surface and a lower surface;
   (c) an extension extending integrally from said bottom surface of said base;
   (d) a bore positioned substantially centrally in said base;
   (e) said bore extending from said top surface through said extension;
   (f) internal threads in said bore in the area thereof extending through said extension;
   (g) an upright solid medium support extending upwardly from said upper surface of said base;
   (h) a transparent elongated cap for covering said upright solid medium;
   (i) said cap having an open end and a closed end;
   (j) said cap, at the open end thereof, and said base having cooperating connecting means for holding said cap on said base; and
   (k) whereby upon connecting of said internal threads to a liquid culture body, said bore provides connection of the liquid contents of a liquid culture bottle to said solid medium on said upright solid medium support.

2. The device of claim 1, further characterized by
   (a) said cooperating connecting means are external screw threads adjacent the said top surface of said base and internal screw threads adjacent the open end of said cap.

3. The device of claim 1, further characterized by
   (a) said upright solid medium support being integral with said base.

4. The device of claim 1, further characterized by
   (a) solid culture medium positioned on the surface of said upright support.

5. The device of claim 1, further characterized by
   (a) said upright solid medium support is generally u-shaped; and
   (b) a pair of opposed integral flanges with one each positioned at each end of said upright solid medium support.

6. The device of claim 1, further characterized by
   (a) said solid medium support extending from said base upwardly from one side of said bore.

7. The device of claim 1, further characterized by
   (a) a pair of solid medium supports positioned in opposed relation on each side of said bore.

8. The device of claim 7, further characterized by
   (a) each of said upright solid medium supports being generally u-shaped; and
   (b) each of said upright solid medium suports having a pair of opposed integral flanges with one each positioned at each end of said generally u-shaped upright solid medium support.

9. The device of claim 7, further characterized by
   (a) solid culture media positioned on the surfaces of each of said pair of upright supports.

10. An assembly for culturing microorganisms wherein the solid medium is contained separately to the liquid medium after exposure, characterized by
   (a) a liquid culture medium bottle;
   (b) said bottle having a closed end and an open end;
   (c) a neck on said bottle adjacent the open end;
   (d) external threads on said neck; and
   (e) a device for connection to said external threads, said device comprising
      (1) a generally flat base;
      (2) said base having an upper surface and a lower surface;
      (3) an extension extending integrally from said bottom surface of said base;
      (4) a bore positioned substantially centrally in said base;
      (5) said bore extending from said top surface through said extension;
      (6) internal threads in said bore in the area thereof extending through said extension for cooperating with said external threads on said neck allowing momentary contact of said solid medium with said liquid medium with subsequent segregation;
      (7) an upright solid medium support extending upwardly from said upper surface of said base;
      (8) a transparent elongated cap for covering said upright solid medium during culturing;
      (9) said cap having an open end and a closed end; and
      (10) said cap, at the open end thereof, and said base having cooperating connecting means for holding said cap on said base and for exposing said solid medium to examination.

* * * * *